United States Patent [19]
Watson

[11] Patent Number: 5,176,627
[45] Date of Patent: Jan. 5, 1993

[54] IMPLANTABLE FLUID FLOW CONTROL DEVICE HAVING TWO-PIECE BASE, AND ASSEMBLY PROCESS

[75] Inventor: David A. Watson, Goleta, Calif.

[73] Assignee: Pudenz-Schulte Medical Research Corporation, Goleta, Calif.

[21] Appl. No.: 633,081

[22] Filed: Dec. 19, 1990

Related U.S. Application Data

[63] Continuation-in-part of Ser. No. 524,136, May 15, 1990, Pat. No. 5,154,693.

[51] Int. Cl.⁵ .............................. A61M 5/00
[52] U.S. Cl. .............................. 604/8; 604/9; 137/510
[58] Field of Search ...................... 604/8–10, 604/128; 137/510, 522

[56] References Cited

U.S. PATENT DOCUMENTS

| | | |
|---|---|---|
| 4,552,553 | 11/1975 | Schulte et al. |
| 4,560,375 | 12/1985 | Schulte et al. ............ 604/9 |
| 4,636,194 | 1/1987 | Schulte et al. |
| 4,741,730 | 5/1988 | Dormandy, Jr. et al. ........ 604/8 |
| 4,781,674 | 11/1988 | Redmond et al. ............ 604/9 |
| 4,795,437 | 1/1989 | Schulte et al. |
| 4,850,955 | 7/1989 | Newkirk ............ 604/9 |
| 4,861,331 | 8/1989 | East et al. |
| 4,867,741 | 9/1989 | Portnoy ............ 604/10 |
| 4,995,864 | 2/1991 | Bartholomew et al. ............ 604/153 |

Primary Examiner—Robert A. Hafer
Assistant Examiner—Kerry Owens
Attorney, Agent, or Firm—Kelly, Bauersfeld & Lowry

[57] ABSTRACT

An implantable fluid flow control device is assembled in a process wherein a first base is provided having a snap-fit barbed connector which defines a fluid passageway and a spline offset from the barbed connector, and a second base having a connector receptacle which defines another passageway and a spline receiving slot. The barbed connector is inserted into the receptacle, and simultaneously the spline is slidably received within the spline receiving slot in a manner preventing tensile and torsional movement between the bases. The coupled bases are placed in a holding fixture, and brought into close proximity with a heated element to fuse the first and second bases together. A pair of housing bodies are placed over, respectively, the first and second bases such that the bases and the housing bodies cooperatively define a fluid flow path through the flow control device. In particular, the housing and the first base cooperate to provide a reservoir for flushing fluid through the device by application of percutaneous manual pressure to the device, and the housing and the second base cooperate to provide a siphon control device. A valve is situated between the flushing reservoir and the siphon control device within the fluid flow path to control passage of fluid through the device.

20 Claims, 3 Drawing Sheets

FIG. 10 ing description, the present invention satisfies these needs and provides other related advantages.

IMPLANTABLE FLUID FLOW CONTROL DEVICE HAVING TWO-PIECE BASE, AND ASSEMBLY PROCESS

RELATED APPLICATION

This is a continuation-in-part application of U.S. patent application Ser. No. 07/524,136, filed May 15, 1990 now U.S. Pat. 5,154,693 and entitled FLOW CONTROL DEVICE HAVING SELECTABLE ALTERNATIVE FLUID PATHWAYS.

BACKGROUND OF THE INVENTION

This invention relates generally to a surgically implantable physiological shunt systems and related flow control devices. More particularly, the present invention relates to shunt systems including one-way flow control devices for controlling the flow of cerebrospinal fluid out of a brain ventricle and preventing backflow of fluid into the brain ventricle, and processes for manufacturing such devices.

In the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids accumulate within the skull and exert extreme pressure and skull deforming forces.

In treating hydrocephalus, cerebrospinal fluid accumulated in the brain ventricles is typically drained away utilizing a drainage or shunt system including a catheter inserted into the ventricle through the skull, which is connected to a tube which conducts the fluid away from the brain to be reintroduced into the peritoneal cavity or into the vascular system, as by extending a distal catheter through the patient's jugular vein to the atrium portion of the heart. To control the flow of cerebrospinal fluid and maintain the proper pressure in the brain ventricle, a pump or valve is placed in the conduit between the brain and the peritoneal cavity or the heart. An exemplary flow control device is found in U.S. Pat. No. 4,560,375.

Although such drainage systems have provided successful results, a problem of over drainage of the cerebrospinal fluid from the brain ventricles sometimes exists. Over drainage of cerebrospinal fluid may result in excessive reduction of the cerebrospinal fluid pressure within the brain ventricles and predispose the development of a subdural hematoma or hydroma, and excessive reduction of ventricular size leading to shunt obstruction because of impingement of the ventricular walls on the inlet holes of the ventricular catheter. This over drainage can be caused by the siphoning effect of hydrostatic pressure in the distal shunt catheter. The siphoning effect of hydrostatic pressure may be created by the elevation of the ventricular catheter inlet with respect to the distal catheter outlet (i.e., when the patient sits, stands or is held erect). In order to prevent such over drainage caused by the siphoning effect of hydrostatic pressure in the distal shunt catheter, siphon control devices have been placed in the conduit, typically between the flow control device and the peritoneal cavity or the heart. An exemplary siphon control device is found in U.S. Pat. No. 4,795,437.

In the past, a physician desiring to include both a flow control device having a pump or valve, and a siphon control device has been required to link the two separate components by surgical tubing or the like during the surgical procedure. The addition of separate flow control elements into a shunt system has several drawbacks, including the lengthening of surgery time required to implant the shunt system, compatibility problems of devices produced by different manufacturers, and the introduction of potential shunt separation and/or leak sites where the separate components are connected to one another via the surgical tubing.

In order to solve these and other related problems, it has been proposed to combine two or more functional elements into a single fluid flow control device. It has been found, however, that such combination-type flow control devices cannot be manufactured as an integral unit utilizing standard medical implant manufacturing techniques.

Accordingly, there has been a need in the medical arts for an implantable fluid flow control device which can be assembled in accordance with a simplified process to provide the flow control characteristics previously obtainable only by connecting, in series, two or more shunt system devices. Such physiological drainage devices for controlling the flow of fluid from one part of the body to another must be relatively inexpensive to manufacture and capable of being constructed substantially of non-metallic parts which are not subject to adhering to one another and causing a malfunction of the device. A combination flow control device is needed which includes a one-way flow control valve for controlling the flow of cerebrospinal fluid out of the brain ventricle and preventing backflow of fluid into the brain ventricle, and permits fluid flow therethrough only when upstream fluid pressure exceeds downstream fluid pressure by a selected pressure differential.

Additionally, a novel assembly process for flow control devices utilized in physiological shunt systems is needed wherein separate functional components of the device can be manufactured separately and assembled together in a simplified procedure to produce a reliable and economical product. Such a device may utilize two separate functional bases which can be connected to one another in a manner ensuring no relative tensile or torsional movement, and invested within a housing to define the desired fluid flow path through the device. Such an assembly process should minimize the possibility of any unintended fluid leakage from the device, and preferably require no adhesive to secure the bases to one another. As will become apparent from the following description, the present invention satisfies these needs and provides other related advantages.

SUMMARY OF THE INVENTION

The present invention resides in a physiological shunt system for controlling the flow of fluid from one part of the body to another, which is constructed substantially of non-metallic materials, provides trouble-free, reliable operation in use, and combined the functions of several flow control shunt components into a single unit/device. The shunt system of the present invention is relatively inexpensive to manufacture and can be easily modified to accommodate a range of desired pressure/flow characteristics. In accordance with the present invention, a fluid flow control device for use in a subcutaneously implantable physiological shunt system includes a proximal base and a distal base, means for connecting, without the use of adhesives, the proximal base to the distal base in a manner ensuring no relative tensile or torsional movement of the bases, and a housing generally surrounding the proximal and distal bases. The housing defines, in connection with the bases, a fluid flow path through the device from an inlet to an outlet, and a valve is provided within the fluid flow path for controlling fluid flow through the device.

The fluid flow control device is assembled utilizing a manufacturing process wherein the bases are provided with interactive locking members which define fluid passageways through the bases. These locking members fluidly couple the fluid passageways through the bases and mechanically attach the bases in a manner limiting relative movement thereof. The bases are spot welded to fuse them together, and then are assembled within the flexible housing such that the bases and the housing cooperatively define the fluid flow path through the device.

In a preferred form of the invention, the process for manufacturing an implantable fluid flow control device involves the assembly of a two-piece base. The first base includes first and second fluid passageways therethrough, a snap-fit barbed connector which defines the second fluid passageway, and a spline which is offset from the barbed connector but extends generally parallel thereto. The second base includes third and fourth fluid passageways therethrough, a connector receptacle defining the third fluid passageway, and a spline receiving slot. The snap-fit barbed connector is inserted into the connector receptacle to fluidly couple the second and third fluid passageways and to mechanically attach the first base to the second base. The connector and the receptacle interlock to prevent disassociation of the bases by limiting or preventing tensile movement therebetween. Simultaneously, the spline is slidably received within and substantially enveloped by the spline receiving slot in a manner limiting torsional movement between the bases.

After the first and second bases have been mechanically attached to one another, they are spot welded to form a permanent coupling. In this regard, the coupled bases are placed in a holding fixture, and a heated element is brought into close proximity with the spline. The spline is melted into the spline receiving slot such that the first and second bases are fused together.

The fused first and second bases are assembled within a housing such that the bases and the housing cooperatively define a fluid flow path extending from the first fluid passageway forming an inlet of the fluid flow control device, to the fourth fluid passageway forming an outlet of the fluid flow control device. The housing and the first base cooperate to provide means for flushing fluid through the fluid flow control device by application of percutaneous manual pressure to the device. The housing and the second base cooperate to provide a siphon control device which prevents fluid flow through the fluid flow control device in the absence of positive upstream fluid pressure on the device, or in response to negative hydrostatic downstream pressure on the device. A valve diaphragm is situated between the flushing means and the siphon control device within the fluid flow path.

The housing preferably includes a first housing body and a second housing body. The coupled bases are inserted into the second housing body such that the second base is substantially enveloped therein. The coupled bases are similarly inserted into the first housing body such that the first base is substantially enveloped therein. A portion of the first housing body overlaps a portion of the second housing body, and overlapping portions of the first and second housing bodies are sealed to one another. The portion of the second housing body which overlaps the base is sealed thereto. The sealing step includes securing the overlapping portion of the second housing body to one of the bases by means of an over-suture, and injecting a silicone adhesive between the overlapping portions of the first and second housing bodies.

The resultant fluid flow control device includes means for occluding the first passageway by application of percutaneous manual pressure to the device. A fifth passageway is provided through the first base, wherein a portion of the first base surrounding the fifth passageway provides a valve seat for the valve. The valve includes a flow control member attached to the first base which contacts the valve seat in a manner normally occluding the fifth passageway, but which selectively opens to permit controlled unidirectional flow therethrough. More specifically, the flow control member includes a central support and a resilient membrane. The central support is attached to the first base and extends therefrom to support the resilient membrane. The resilient membrane is generally arch-shaped and has a portion thereof capable of engaging the valve seat to occlude the valve passageway. Means are provided for occluding the fifth passageway by application of percutaneous manual pressure to the device.

In order to provide desired resistance to adhesion between various components of the flow control device, particularly during storage, rigid components of the device are generally formed of a rigid polypropylene material, while elastic components, such as the valve membrane and the housing, are preferably molded of a silicone elastomer material.

The siphon control device comprises a pair of spaced, substantially parallel, flexible diaphragms provided by the second housing body, and the second base invested within the second housing body. The second base and second housing body define a fluid flow pathway between the valve diaphragm and the outlet of the device.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

As shown in the drawings for purposes of illustration, the present invention is concerned with an improved flow control device, generally designated in the accompanying drawings by the reference number 20. The improved flow control device 20 is intended for use in a surgically implanted physiological shunt system for draining fluid from one portion of the body to another. In order to connect, for example, the device 20 in such a system, the device includes an inlet connector 22 and an outlet connector 24 which each receive one end of a piece of surgical tubing (not shown). The ends of the surgical tubing are placed over the connectors 22 and 24 and secured thereon by a single ligature just inside an annular ridge 26 formed near the end of each connector.

When the flow control device 20 is used in a drainage system intended for the treatment of hydrocephalus, the inlet connector 22 is fluidly connected with a proximal catheter which is inserted through the skull into a brain ventricle containing cerebrospinal fluid under pressure. The outlet connector 24 is fluidly connected to a distal catheter which serves to discharge cerebrospinal fluid into, for example, the atrium portion of a patient's heart. Ordinarily the flow control device 20 will be surgically implanted on the patient's skull with a flap of skin overlying the device. To facilitate holding the device in its extended position after implantation, a generally flexible mounting pad 28 can be provided with one or more suture holes.

As will become apparent from the following description, the present invention provides a highly reliable flow control device having a two-piece base, which combines the functions of simple flow control valves with that of a siphon control device. The present invention provides a highly reliable flow control device designed to prevent valve seat deformation and membrane to valve seat sticking, and facilitate implantation by eliminating components to be connected or adjusted other than the surgical tubing to the device itself. Moreover, the present invention provides a simplified assembly process which permits a device to be manufactured that incorporates several different flow control functions.

In accordance with the present invention, the flow control device 20 includes a pair of relatively rigid, molded plastic bases 30 and 32 invested within a resiliently flexible housing 34 which, together, define a fluid flow path through the housing from the inlet connector 22 to the outlet connector 24. A normally closed valve 36 is provided within the fluid flow path to restrict the flow of fluid through the device 20. The housing 34 and the second base 32 cooperate to provide a siphon control device 38 situated between the valve 36 and the outlet connector 24, which prevents fluid flow through the device 20 in the absence of positive upstream fluid pressure or in response to negative downstream hydrostatic pressure on the device. Further, the housing 34 and the first base 30 cooperate to define a pump or flushing reservoir 40 between the inlet connector 22 and the valve 36.

As shown best in FIGS. 2 through 8, the bases 30 and 32 interfit with one another and are integrally formed with, respectively, the inlet and outlet connectors 22 and 24. The first or proximal base 30 is integrally formed with the inlet connector 22 and defines an inlet flow channel 42 extending through the inlet connector 22 to an upwardly facing inlet occluder port 44. The first base forms a bottom plate 46 for the flushing reservoir 40, a support 48 for the valve 36, and a snap-fit interlocking barbed connector 50.

The support 48 defines an outlet chamber 52 for the first base 30 into which the valve 36 extends. The support 48 includes a centrally positioned valve-supporting aperture 54, and three surrounding apertures 56 which permit fluid flow from an upper surface of the support 48 into the outlet chamber 52. An intermediate flow channel 58 extends from the outlet chamber 52 through the connector 50 to direct fluids from the first base 30 to the second base 32.

The barbed connector 50 extends from the base generally opposite to the inlet connector 22, and is supported by a housing support member 60. A pair of splines 62 extend from the housing support member 60 generally parallel to the longitudinal axis of the connector 50 and the intermediate flow channel 58. The connector 50 and the splines 62 interact with corresponding portions of the second base 32 to prevent tensile and torsional movement of the proximal and distal bases 30 and 32 with respect to one another.

In this regard, the second or distal base 32 is integrally formed with the outlet connector 24 which defines an outlet flow channel 64 therethrough. The second or distal base 32 defines a portion of the siphon control device 38. A connector receptacle 66 is provided in the proximal end of the second base 32 for receiving the barbed connector 50 therein (see FIGS. 4 and 5). Spline receiving slots 68 are also provided in the proximal end of the second base, to slidably receive and substantially envelope the splines 62 as the connector 50 is inserted into the receptacle 66.

The flexible housing 34 is provided in two parts: a first or inlet housing body 34a into which the first base 30 is invested, and an outlet or second housing body 34b which is sealed by a suitable adhesive 70 to the inlet housing body 34a in order to provide a continuous elastomeric exterior to the device 20, with the exception of the inlet and outlet connectors 22 and 24 which extend therefrom. The inlet housing body 34a is integrally formed with the mounting pad 28 and includes an inlet aperture through which the inlet connector 22 extends, an inlet occluder wing 72 which generally overlies the inlet occluder port 44, a resiliently flexible dome 74 for the flushing reservoir 40, and a distal occluder wing 76 generally overlying the support 48.

In order to provide a fluid-tight seal between the inlet connector 22 and the housing 34a, a tube 78 is placed over a portion of the inlet connector and secured in place by means of an over-suture 80. A silicone adhesive 82 is then injected into the remaining gap between the housing 34a and the inlet connector 22. This same sealing arrangement is utilized between the housing 34b and the outlet connector 24.

The inlet occluder wing 72 is positioned over the inlet occluder port 44 to facilitate occluding the inlet flow channel 42 at the port 44 by pressing the wing 72 downwardly. Depressing the wing 72 and occluding the port 44 prevents proximal fluid flow from the flushing reservoir 40, defined by the dome 74 and the bottom plate 46, when the dome is pressed downwardly by manual percutaneous pressure. The dome 74 is preferably molded of a silicone elastomer material and is designed to permit injection into the flow control device 20 by a hypodermic needle through the dome. The bases 30 and 32 are preferably molded of a polypropylene material which provides sufficient rigidity to prevent a needle from inadvertently passing through the device 20 if an injection is made into the flushing reservoir 40. The construction of the bases 30 and 32 and the housing 34 helps to guide a physician in manually percutaneously manipulating the device 20 when subcutaneously implanted, for purposes of flushing the shunt system.

The distal occluder wing 76 is positioned over the support 48 for the valve 36 to facilitate occluding the apertures 56. This is accomplished by pressing the wing 76 downwardly, which effectively prevents distal fluid flow from the flushing reservoir 40 when the dome is pressed downwardly by manual percutaneous pressure.

The outlet housing body 34b surrounds a portion of the second base 32 to define the siphon control device 38 which is similar to that shown and described in U.S. Pat. No. 4,795,437, the contents of which are incorporated herein by reference. The siphon control device 38 includes an outer wall 84 and an inner wall 86 which is situated within and encircled about by the outer wall. The intermediate flow channel 58 directs fluid from the outlet chamber 52 to a central SCD reservoir 88 defined as the area between the inner wall 86 and the outer wall 84. The outlet flow channel 64 extends through the inner wall 86 to the distal end of the outlet connector 24.

Figures 9, 10, 11:
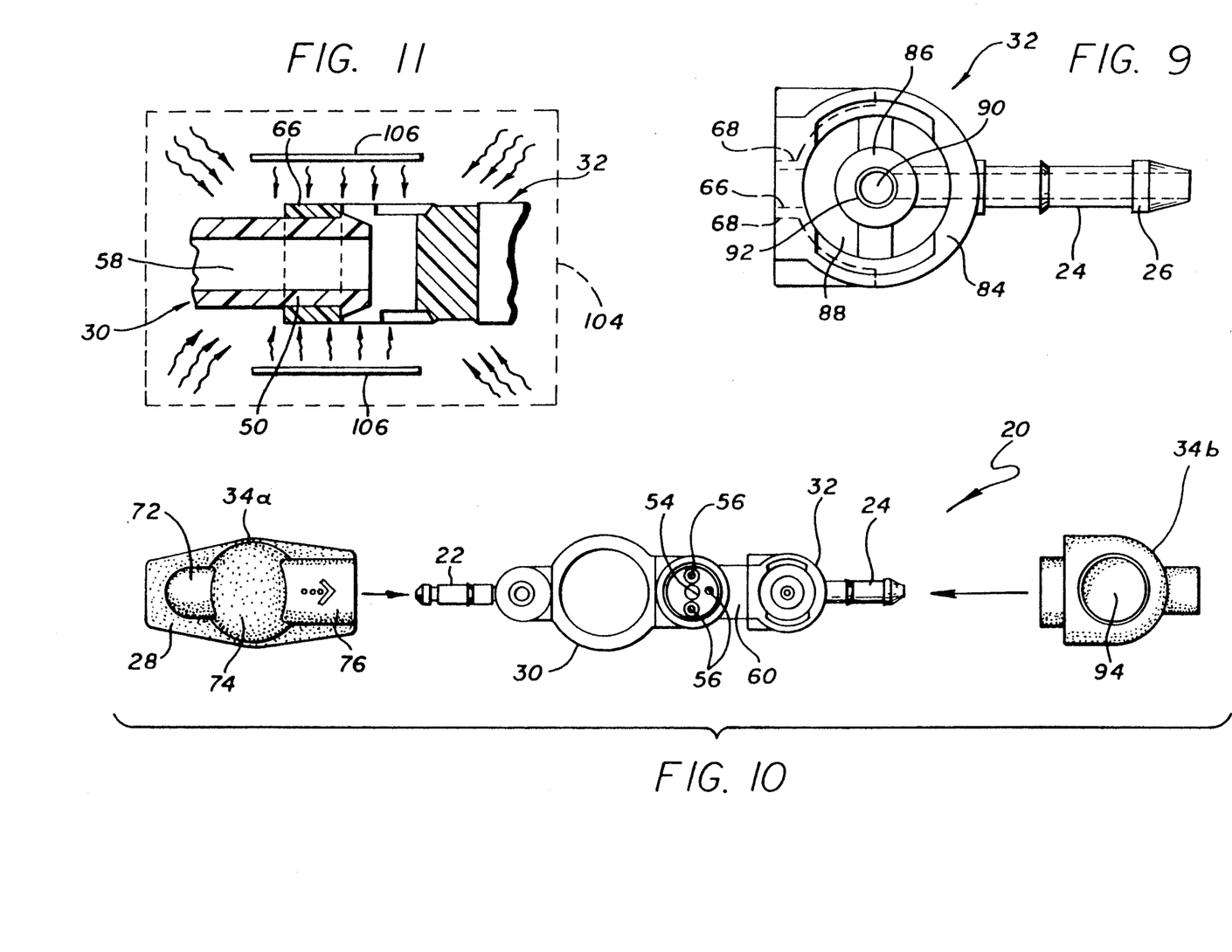
FIG. 9 is a top plan view of the distal base, taken generally along the line 9—9 of FIG. 3.
FIG. 10 is a top plan assembly diagram, illustrating assembly of two housing bodies onto the fused proximal and distal bases.
FIG. 11 is a schematic illustration of a spot welding step utilized to fuse the proximal and distal bases to one another, wherein the bases are placed within a holding fixture and a heated element is brought into close proximity with the splines to fuse portions of the proximal base into portions of the distal base.

As can be seen best in FIG. 9, the outer wall 84 is generally circular in shape, and is spaced from and encircles the inner wall 86. The inner wall is also generally circular in shape, and defines an SCD outlet chamber 90 which is adjacent to and in fluid communication with the outlet flow channel 64. The inner wall 86 is constructed to have substantially parallel upper and lower seating surfaces 92, and it effectively forms a barrier separating the SCD reservoir 88 from the SCD outlet chamber 90.

The outlet housing body 34b is provided with a pair of spaced, substantially parallel, flexible elastic diaphragms 94 which are fixed about their peripheries adjacent to the outer wall 84. Each diaphragm has an inner surface which defines the upper and lower limits of the SCD reservoir 88 and the SCD outlet chamber 90, and an outer surface which forms an exterior surface of the siphon control device 38. The diaphragms 94 are situated on opposite sides of the inner wall 86 to position a portion of each inner surface thereof in contact with an adjacent one of the seating surfaces 92 and form a seal therebetween which prevents fluid flow between the outlet chamber 52 and the outlet flow channel 64.

The second housing body 34b further includes integral offset rings 96 which surround each diaphragm 94 to inhibit overlying tissue from occluding the siphon control device 38 when implanted into a patient. An aperture is provided through the housing 34b through which the outlet connector 24 extends. A fluid tight seal is effected between the housing outlet aperture and the outlet connector 24 utilizing a tube 78, an over-suture 80 and an adhesive 82, as described above in connection with the inlet housing body 34a and the inlet connector 22.

In use, the diaphragms 94 normally lie against and interact with the seating surfaces 92 of the inner wall 86 to close the device 20 to fluid flow. The diaphragms 94 move away from the seating surfaces 92, however, in response to a minimal level of positive fluid pressure within the SCD reservoir 88 to permit passage of fluid from the intermediate flow channel 58 to the outlet flow channel 64. The diaphragms 94 close and seal upon the seating surfaces 92 once again in the absence of such positive upstream fluid pressure, or in response to negative downstream hydrostatic pressure in the SCD outlet chamber 90. The siphon control device 38 thus minimizes the undesirable consequences attendant to excessive over drainage of fluid due to the siphoning effect of hydrostatic pressure.

The normally closed valve 36 extends from the support 48 into the outlet chamber 52 for controlling the flow of cerebrospinal fluid out of a brain ventricle. The normally closed valve 36 includes a central support 98 and a resilient membrane 100 molded of a synthetic polymer material different from the material of the first base 30. The resilient membrane 100 is normally biased to close communication between the flushing reservoir 40 and the outlet chamber 52, but will open to permit flow through the apertures 56 when the pressure on the inlet or proximal side of the resilient membrane exceeds the pressure on the outlet or distal side by a predetermined amount. Moreover, should the pressure on the distal side of the resilient membrane 100 ever exceed the pressure on the proximal side, tending to cause flow in a reverse direction through the normally closed valve 36, the membrane 100 will seal tightly against a valve seat 102 provided on the support 48, to prevent any such reverse fluid flow.

The first base 30 is preferably formed of a polypropylene material, and the membrane 100 is preferably formed of a silicone elastomer material. Both polypropylene and elastomer materials have been shown to produce an acceptable level of tissue reaction, and the use of this particular duality of materials, in contrast to the use of only a single material, markedly decreases the chance of the membrane 100 adhering to any portion of the valve seat 102 which would clog the fluid pathway through the device 20 and defeat the purpose of the device.

An added advantage of using these particular materials is the avoidance of the negative effect of metal components, due to radiation scatter or "sunburst effect," on films taken by, for example, computerized axial tomography (CAT) scanning equipment. This type of scanning frequently accompanies the use of surgically implanted flow control valves, and the absence or limitation of metal in the areas scanned will permit more accurate and complete results to be gathered from CAT scanning.

The membrane 100 has an arch-shape, as for example a section of a sphere, and is designed to contact the valve seat 102 generally along the outer edges of the membrane in a manner surrounding the apertures 56. The membrane 100 is secured in place adjacent to the valve seat 102 by the central support 98 which is fixed within the valve aperture 54. A needle guard disc 103 is adhesively secured in place opposite the support 48, to generally enclose the outlet chamber 52.

Since the normally closed valve 36 is primarily designed to provide controlled resistance to cerebrospinal fluid flow from a brain ventricle to another location in the body, it will be appreciated that a doctor must be able to select a valve having the particular pressure/flow characteristics desired for each individual application. That is, a valve which permits flow at a relatively low pressure differential may not be suitable where the maintenance of a higher pressure differential is indicated. Toward this end, in order to provide a variety of valves having different pressure/flow characteristics, the valve 36 can be provided with a thick membrane 100 or a relatively thin membrane. Resistance to flow increases with the increase in membrane thickness.

The design of the flow control device 20 described above lends itself to easy percutaneous distal and proximal flushing. In order to flush the device 20 distally, the inlet occluder wing 72 is pressed downwardly to occlude the inlet occluder port 44. The dome 74 is then simply pressed downwardly to flush the contents of the flushing reservoir 40 past the normally closed valve 36, through the intermediate flow channel 58, then past the siphon control device 38 and through the outlet flow channel 64. Similarly, proximal flushing can be accomplished by pressing downwardly on the distal occluder wing 76 to occlude the apertures 56 through the support 48. The dome 74 is then pressed downwardly to flush fluid proximally from the flushing reservoir 40 out of the device 20 through the inlet flow channel 42.

A feature of the present invention lies in the process for manufacturing the implantable fluid flow control device 20 having, initially, separable bases 30 and 32. In accordance with this process, the first base 30 includes first and second fluid passageways therethrough corresponding to, respectively, the inlet flow channel 42 and the intermediate flow channel 58. The snap-fit barbed connector 50 defines a portion of the intermediate flow channel 58, and further a pair of splines 62 are offset from the barbed connector and extend generally parallel thereto. The second base 32 includes third and fourth fluid passageways corresponding, respectively, to the connector receptacle 66 and the outlet flow channel 64. Further, spline receiving slots 68 are provided for slidably receiving the splines 62 as the bases are mated to one another.

To fluidly couple the second and third fluid passageways and to mechanically attach the first base 30 to the second base 32, the connector 50 is inserted into the receptacle 66. Simultaneously, the splines 62 are slidably received within and substantially enveloped by the spline receiving slots 68. This coupling of the first base 30 to the second base 32 limits tensile and torsional movement between the bases, without the use of adhesives.

As illustrated in FIG. 11, after the bases 30 and 32 are coupled to one another, they are placed in a holding fixture 104 (schematically illustrated by the broken box of FIG. 11), and a heated element 106 is brought into close proximity with the splines 62. With the element 106 heated to approximately 700° F., radiant and convective heat transfer melts the splines 62 into the spline receiving slots 68, such that the first and second bases 30 and 32 are fused to one another.

The normally closed valve 36 is secured within the valve aperture 54 provided through the support 48, and then the needle guard disc 103 is secured in place relative to the first base 30 below the outlet chamber 52.

Figure 1:
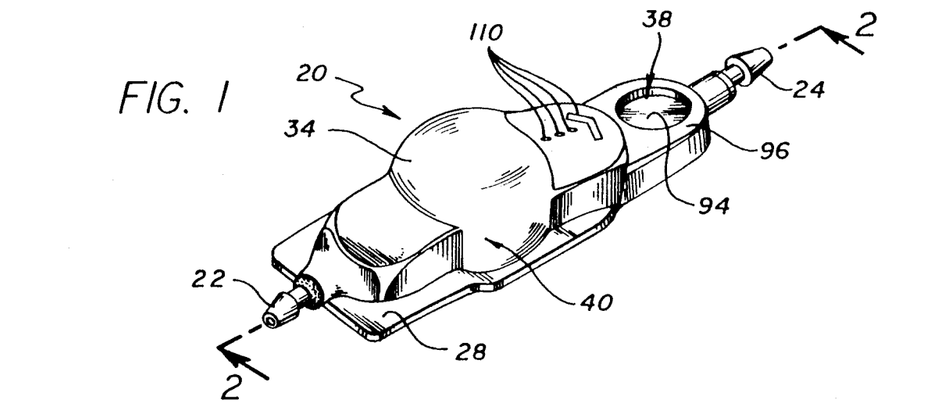
FIG. 1 is a perspective view of an implantable fluid flow control device having a two-piece base embodying the invention.
Figure 2:
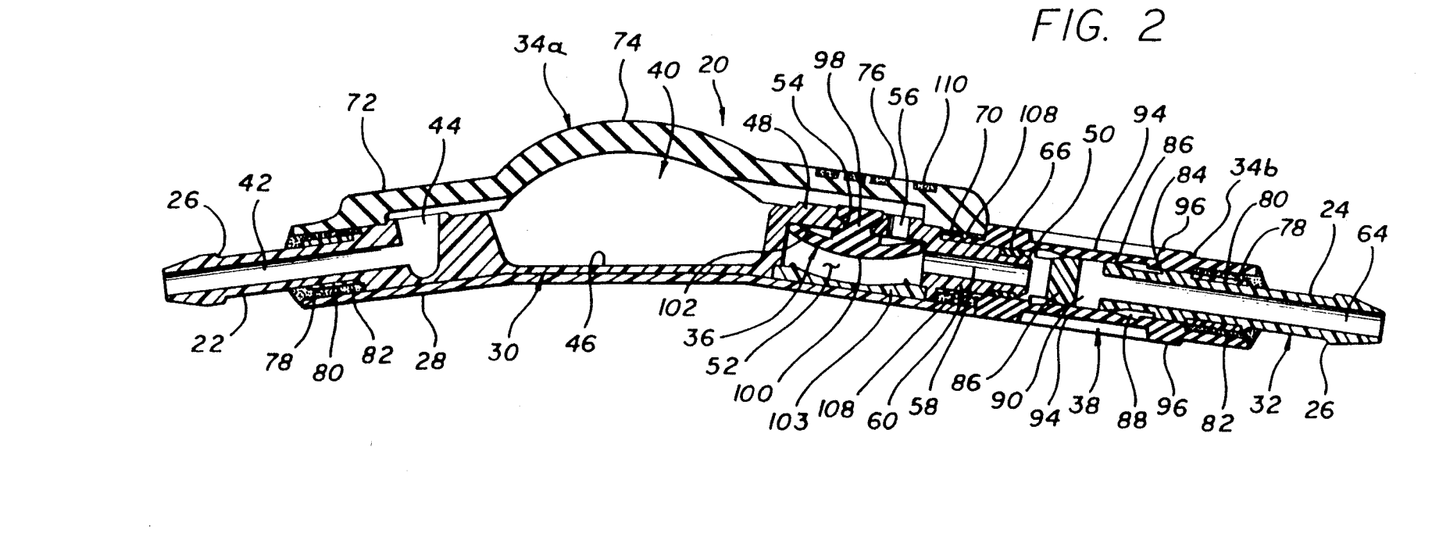
FIG. 2 is an enlarged vertical section taken generally along line 2—2 of FIG. 1.
Figure 3:
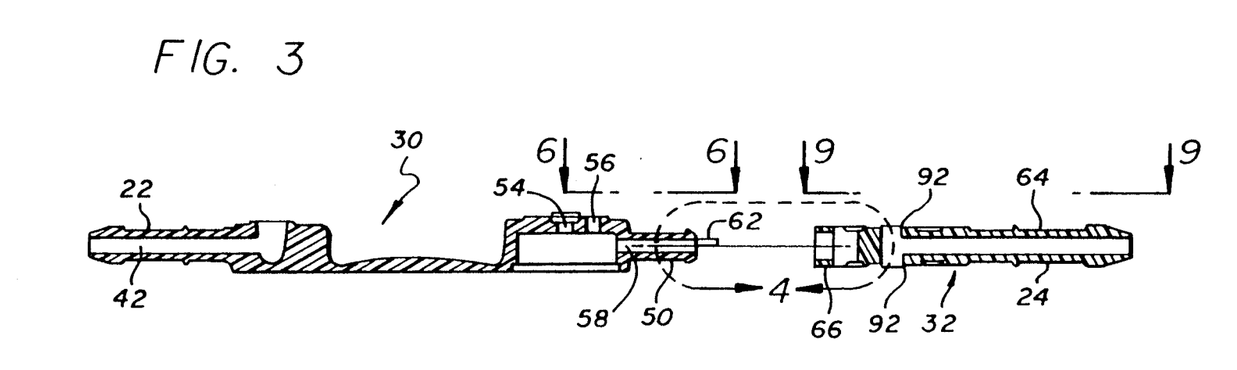
FIG. 3 is an exploded vertical sectional view of the proximal and distal bases, shown in assembled form in FIG. 2.
Figures 4, 5, 6, 7, 8:
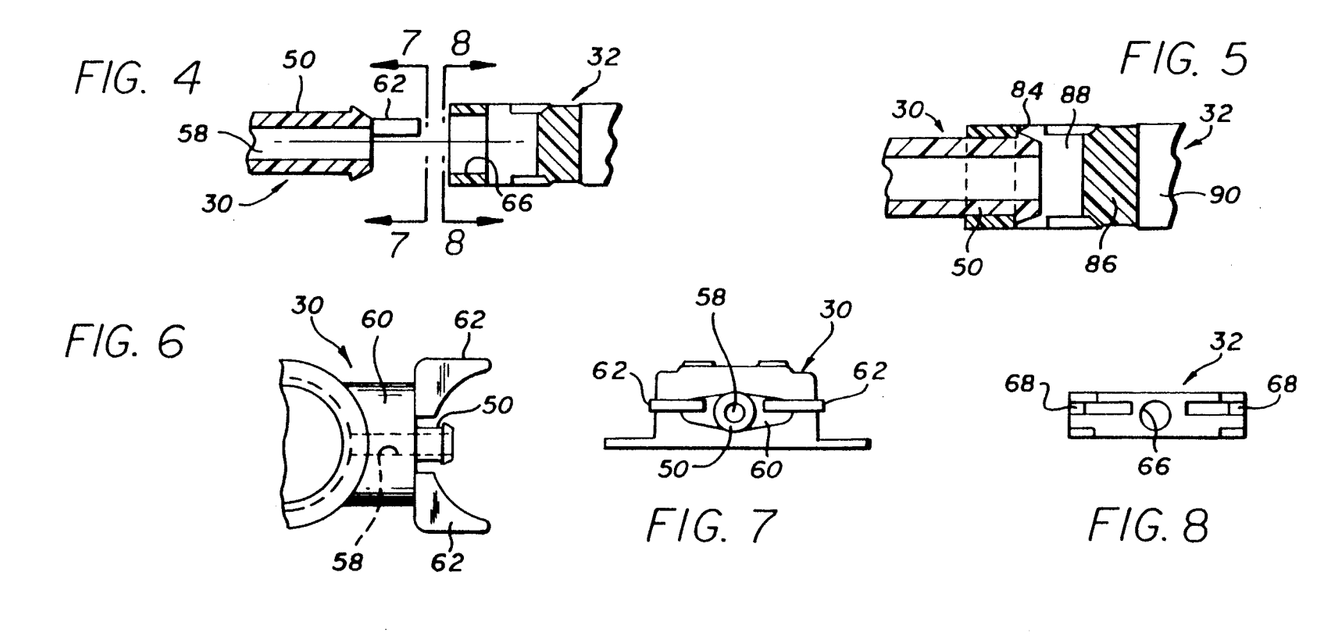
FIG. 4 is an enlarged, fragmented vertical section of those portions of the proximal and distal bases illustrated by the line 4—4 of FIG. 3, illustrating the alignment of a snap-fit interlocking barbed connector provided on the proximal base, with a corresponding connector receptacle provided in the distal base.
FIG. 5 is a fragmented sectional view similar to FIG. 4, illustrating the interlocking configuration of the connection between the proximal and distal bases after the snap-fit barbed connector is inserted into the connector receptacle.
FIG. 6 is a fragmented top plan view taken generally along the line 6—6 of FIG. 3, illustrating the distal end of the proximal base, and particularly the provision of two splines relative to the snap-fit interlocking barbed connector.
FIG. 7 is an elevational view of the distal end of the proximal base, taken generally in the direction of line 7—7 of FIG. 4.
FIG. 8 is an elevational view of the proximal end of the distal base, taken generally in the direction of line 8—8 of FIG. 4.

As shown best in FIGS. 2 and 10, the fused bases 30 and 32 are then assembled within the housing 34 such that the bases and the housing cooperatively define a fluid flow path through the flow control device 20 extending from the inlet flow channel 42 to the outlet flow channel 64. Preferably the coupled bases are first inserted into the second or distal housing body 34b such that the second base 32 is substantially enveloped therein. A single ligature 108 is tied about a proximal end of the second housing body 34b to seal that portion of the second housing body 34 to the underlying housing support member 60. The coupled bases 30 and 32 are then inserted into the first or proximal housing body 34a such that the first base 30 is substantially enveloped therein. A distal end portion of the first housing body 34a overlaps the proximal end portion of the second housing body 34b, and these overlapping portions of the housing bodies are sealed to one another utilizing the housing adhesive 70.

If desired, radiopaque indicators 110 can be embedded into the upper surface of the housing 34.

From the foregoing it is to be appreciated that the present invention provides a flow control device 20 for use in a subcutaneously implanted physiological shunt system. The device 20 utilizes two bases 30 and 32 which can be joined together without the use of adhesives in a manner preventing tensile and torsional movement of one base with respect to the other. This simplifies the assembly process of the device, and provides a reliable and economical valve for use by surgeons. The construction of the flow control device of the present invention permits selective distal and proximal flushing of the device through the application of manual percutaneous pressure. Further, the present invention provides a device by which the flow of cerebrospinal fluid out of a brain ventricle can be controlled while preventing the backflow of fluid into the brain ventricle, and which inhibits excessive drainage through the physiological shunt in the presence of excessive downstream suction.

Although a particular embodiment of the invention has been described in detail for purposes of illustration, various modifications may be made without departing from the spirit and scope of the invention. Accordingly, the invention is not to be limited, except as by the appended claims.

I claim:

1. A fluid flow control device for use in a subcutaneously implantable physiological shunt system, comprising:
    a proximal base having a first passageway for fluids entering the fluid flow control device, and a second passageway for fluid exiting the proximal base;
    a distal base having a third passageway for receiving fluids exiting the proximal base through the second passageway, and a fourth passageway for fluids exiting the fluid flow control device;

means for mechanically connecting the proximal base and the distal base, and for fluidly coupling the second and the third passageways to limit tensile movement between the bases;

a housing generally surrounding the proximal and distal bases to define, in connection with the bases, a fluid flow path through the fluid flow control device; and a valve within the fluid flow path for controlling fluid flow through the device.

2. A fluid flow control device as set forth in claim 1, wherein the connecting means includes a snap-fit connector defining the second passageway, and a complementary connector receptacle defining the third passageway, such that insertion of the connector into the receptacle interlocks the proximal base and the distal base.

3. A fluid flow control device as set forth in claim 2, including means for preventing disassociation of the proximal and distal bases after the connector is inserted into the receptacle.

4. A fluid flow control device as set forth in claim 2, wherein the connecting means includes means for preventing torsional movement of the proximal base with respect to the distal base once the connector is inserted into the receptacle.

5. A fluid flow control device as set forth in claim 4, wherein the torsional movement preventing means includes a spline fixed to one of the bases and a spline receiving slot provided in the other base to which the spline is not fixed, such that the spline is slidably received and substantially enveloped by the spline slot as the connector is inserted into the receptacle.

6. A fluid flow control device as set forth in claim 4, wherein the housing and the proximal base cooperate to provide means for flushing fluid through the fluid flow control device by application of percutaneous manual pressure to the device and wherein the housing and the distal base cooperate to provide a siphon control device which prevents fluid flow through the fluid flow control device in the absence of positive upstream fluid pressure through the device or in response to negative hydrostatic downstream pressure on the device.

7. A fluid flow control device as set forth in claim 6, wherein the valve is situated between the flushing means and the siphon control device, and wherein the fluid flow control device includes means for occluding the first and fourth passageways by application of percutaneous manual pressure to the housing.

8. A fluid flow control device as set forth claim 6, wherein the proximal base includes a valve seat surrounding a fifth passageway through the proximal base, and wherein the valve includes a flow control member attached to the proximal base and contacting the valve seat to normally occlude the fifth passageway but selectively open to permit controlled unidirectional flow therethrough.

9. A fluid flow control device for use in a subcutaneously implantable physiological shunt system, comprising:

a rigid proximal base having a first passageway for fluids entering the fluid flow control device, and a second passageway for fluid exiting the proximal base;

a rigid distal base having a third passageway for receiving fluids exiting the proximal base through the second passageway, and a fourth passageway for fluids exiting the fluid flow control device;

means for connecting, without the use of adhesives, the proximal base to the distal base, the connecting means including a snap-fit barbed connector defining the second passageway, and a complementary connector receptacle defining the third passageway, such that insertion of the connector into the receptacle interlocks the proximal base and the distal base and prevents dissociation of the proximal and distal bases after the connector is inserted into the receptacle;

a flexible housing generally surrounding the proximal and distal bases to define, in connection with the bases, a fluid flow path through the fluid flow control device, wherein the housing and the distal base cooperate to provide means for flushing fluid through the fluid flow control device by application of percutaneous manual pressure to the device, and wherein the housing and the distal base cooperate to provide a siphon controlled device which prevents fluid flow through the fluid flow control device in the absence of positive upstream fluid pressure through the device or in response to negative hydrostatic downstream pressure on the device; and a valve situated between the flushing means and the siphon control device.

10. A fluid flow control device as set forth in claim 9, wherein the connecting means includes a spline affixed to one of the bases and a spline receiving slot provided in the other base to which the spline is not fixed, such that the spline is slidably received and substantially enveloped by the spline receiving slot as the connector is inserted into the receptacle.

11. A fluid flow control device as set forth in claim 10, including means for occluding the first passageway by application of percutaneous manual pressure to the device, a fifth passageway through the proximal base, wherein a portion of the proximal base surrounding the fifth passageway provides a valve seat for the valve, the valve including a flow control member attached to the proximal base and contacting the valve seat to normally occlude the fifth passageway but selectively open to permit controlled unidirectional flow therethrough, and means for occluding the fifth passageway by application of percutaneous manual pressure to the device.

12. A process for manufacturing an implantable fluid flow control device having a two-piece base, the process steps comprising:

providing a first base having first and second fluid passageways therethrough, and a first locking member, wherein the first locking member defines the second fluid passageway;

providing a second base having third and fourth fluid passageways therethrough, and a second locking member, wherein the second locking member defines the third fluid passageway;

inserting the first locking member into the second locking member to fluidly couple the second and third fluid passageways and to mechanically attach the first base to the second base in a manner limiting tensile movement between the bases;

spot welding the first and second bases to fuse the first and second locking members together; and assembling the first and second bases within a flexible housing such that the bases and the housing cooperatively define a fluid flow path through the flow control device.

13. A process as set forth in claim 12, including the steps of providing the first base with a third locking member and providing the second base with a fourth locking member, wherein, simultaneously with the inserting step, the third locking member is inserted into the fourth locking member to limit torsional movement between the bases.

14. A process as set forth in claim 13, wherein the third locking member comprises a spline and the fourth locking member comprises a spline receiving slot such that during the inserting step the spline is slidably received within and substantially enveloped by the spline receiving slot, and wherein during the spot welding step the third and fourth locking members are fused together.

15. A process as set forth in claim 14, wherein the spot welding step includes the steps of placing the coupled bases in a holding fixture, bringing a heated element into close proximity with the spline, and melting the spline into the spline receiving slot such that the third and fourth locking members are fused together.

16. A process as set forth in claim 12, wherein the assembly step includes the steps of providing a first housing body and a second housing body, inserting the coupled bases into the second housing body such that the second base is substantially enveloped therein, inserting the coupled bases into the first housing body such that the first base is substantially enveloped therein and a portion of the first housing body overlaps a portion of the second housing body sealing the overlapping portions of the first and second housing bodies, and sealing the overlapping portion of the second housing body to one of the bases.

17. A process as set forth in claim 16, wherein the sealing step includes the steps of securing the overlapping portion of the second housing body to one of the bases by means of an over-suture, and injecting a silicone adhesive between the overlapping portions of the first and second housing bodies.

18. A process as set forth in claim 12, wherein the first locking member comprises a snap-fit barbed connector, and the second locking member comprises a complementary connector receptacle, wherein insertion of the connector into the receptacle interlocks the first base and the second base and prevents disassociation of the bases after the connector is inserted into the receptacle.

19. A process as set forth in claim 12, wherein during the assembling step the housing and the first base cooperate to provide means for flushing fluid through the fluid flow control device by application of percutaneous manual pressure to the flow control device, and wherein the housing and the second base cooperate to provide a siphon control device which prevents fluid flow through the flow control device in the absence of positive upstream fluid pressure through the flow control device or in response to negative hydrostatic downstream pressure on the flow control device, the process further including the step of placing a valve between the flushing means and the siphon control device to control fluid flow through the flow control device.

20. A process for manufacturing an implantable fluid flow control device having a two-piece base, the process steps comprising:
providing a first base having first and second fluid passageways therethrough, a snap-fit barbed connector which defines the second fluid passageway, and a spline offset from the barbed connector and extending generally parallel thereto;
providing a second base having third and fourth fluid passageways therethrough, a connector receptacle defining the third fluid passageway, and a spline receiving slot;
inserting the connector into the receptacle to interlock the first base and the second base and prevent disassociation of the bases after the connector is inserted into the receptacle, wherein simultaneously the spline is slidably received within and substantially enveloped by the spline receiving slot in a manner limiting torsional movement between the bases;
spot welding the first and second bases, including the steps of placing the coupled bases in a holding fixture, bringing a heated element into close proximity with the spline, and melting the spline into the spline receiving slot such that the first and second bases are fused together; and
assembling the first and second bases within a housing such that the bases and the housing cooperatively define a fluid flow path through the flow control device extending from the first fluid passageway forming an inlet of the fluid flow control device, to the fourth fluid passageway forming an outlet for the fluid flow control device, wherein the housing and the first base cooperate to provide means for flushing fluid through the fluid flow control device by application of percutaneous manual pressure to the flow control device, and wherein the housing and the second base cooperate to provide a siphon control device which prevents fluid flow through the fluid flow control device in the absence of positive upstream fluid pressure through the flow control device or in response to negative hydrostatic downstream pressure on the flow control device, and wherein a valve is situated between the flushing means and the siphon control device within the fluid flow path.

* * * * *